ns Patent [19]

Suzuki

[11] 3,976,699
[45] Aug. 24, 1976

[54] SULFUR OXIDATION OF OLEFINS TO KETONES

[75] Inventor: Shigeto Suzuki, San Francisco, Calif.

[73] Assignee: Chevron Research Company, San Francisco, Calif.

[22] Filed: Feb. 11, 1975

[21] Appl. No.: 549,242

Related U.S. Application Data

[62] Division of Ser. No. 52,310, July 6, 1970, Pat. No. 3,892,813.

[52] U.S. Cl. .......................... 260/586 R; 260/597 R
[51] Int. Cl.² .......................................... C07C 45/02
[58] Field of Search ..................... 260/597 R, 586 R

[56] References Cited
UNITED STATES PATENTS

| 2,635,119 | 4/1953 | Finch et al. ..................... 260/597 R |
| 2,691,045 | 10/1954 | Hagemeyer ..................... 260/597 R |
| 3,129,253 | 4/1964 | Odioso et al. .................... 260/597 R |

Primary Examiner—James O. Thomas, Jr.
Assistant Examiner—James H. Reamer
Attorney, Agent, or Firm—G. F. Magdeburger; John Stoner, Jr.; T. G. DeJonghe

[57] ABSTRACT

A process is disclosed for the production of ketones from olefinic hydrocarbons and inert derivatives of olefinic hydrocarbons by the controlled reaction of water and sulfur with the olefin. Ammonia and hydrogen sulfide promotes the conversion.

1 Claim, 1 Drawing Figure

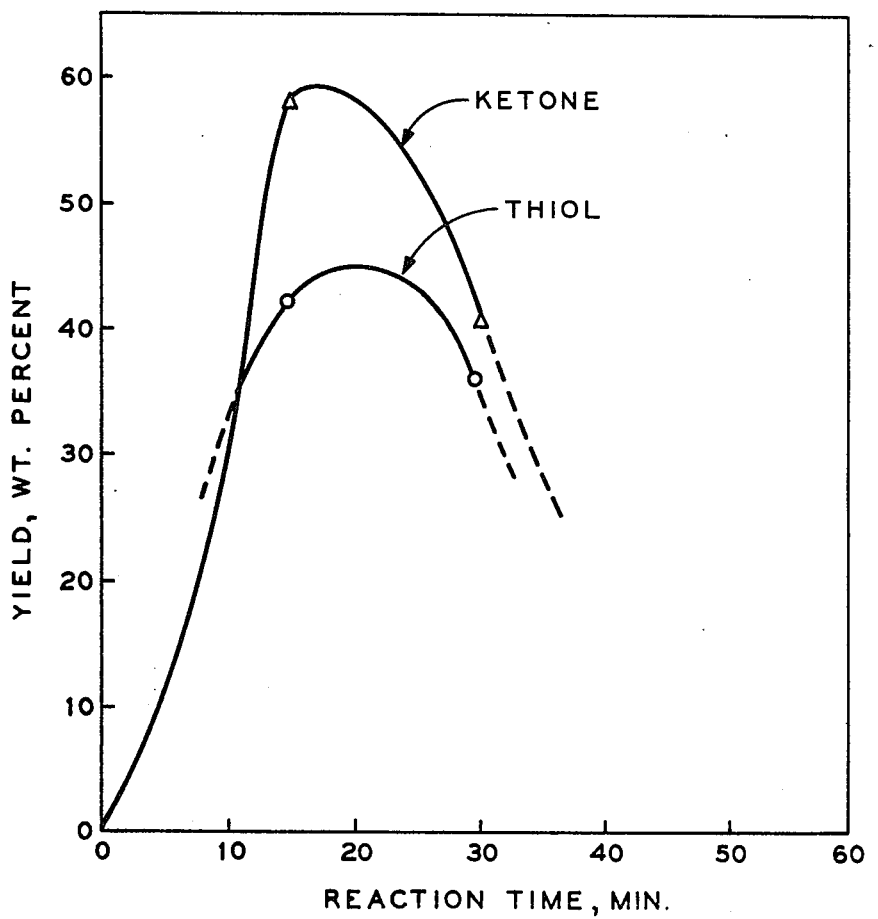

SULFUR OXIDATION OF OLEFINS TO KETONES

This is a division of application Ser. No. 52,310, filed July 6, 1970, now U.S. Pat. No. 3,892,813.

This invention relates to a process for the production of a ketone, and more particularly to the direct conversion of an olefinic hydrocarbon feed to a ketone containing the same number of carbon atoms as the feed compound.

The ketones produced by the subject process are in general well known and have many uses in the chemical art, particularly as solvents, diluents, and the like.

It has now been found that a ketone is produced by heating in the liquid phase a mixture of a mono-olefinic hydrocarbon, water and sulfur at a temperature in the range from about 225° to 325°, preferably 280° to 315°C., provided that for each mol of the olefin the mixture contains an amount of sulfur in the range 0.15 to 2.0 mols, and of water in the range 2 to 100 mols, and further provided that the temperature of the mixture is maintained for a limited time, that is for a period in the range from 5 to 60 minutes. The olefin must be liquefiable at a temperature within the above-described range and contain at least three carbon atoms. At least one of the carbon atoms of the double bond pair must be a secondary carbon atom; in addition, the double bond cannot be included within a six-membered carbocyclic ring.

The main organic components of the resulting product mixture includes the desired ketone and additional amounts of corresponding thiol, and sulfide derivatives of the olefin feed. Upon recycle to the process, these derivatives are in large part converted to the desired ketone product. In the process the conversion of the feed to ketone is promoted by the presence of hydrogen sulfide and of a nitrogen base in the heated mixture, particularly of ammonia.

The production of a ketone as herein is a unique and unexpected result. The oxidation of a ketone to an organic carbocyclic acid and/or acid amide in the manner of Wilgerodt, for example in a system employing aqueous sulfur and ammonia, is well known. Similarly and alternatively, it is known to use an alkene as the feed compound in the Wilgerodt system, thereby producing an organic acid and/or the corresponding amide. Surprisingly, under the particular conditions of the present invention, a mono-olefinic hydrocarbon is converted to the corresponding ketone in very good yield.

The production of ketone from a mono-olefinic hydrocarbon by the subject process may be summarized by the equation:

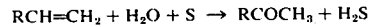

$$RCH=CH_2 + H_2O + S \rightarrow RCOCH_3 + H_2S \quad \text{a.}$$

but the actual reaction mechanism is believed to be complex and to involve a number of chemical equilibria.

The novel production of ketones in the process of the present invention is critically dependent upon several process variables including temperature, reaction duration, and the relative amounts of sulfur and olefin employed in the process. Of secondary and yet substantial importance as factors facilitating the achievement of useful ketone production is the employment of a basic nitrogen compound and hydrogen sulfide as promoters for the desired conversion.

The production of a ketone from an olefin is especially dependent upon the temperature at which the reaction is carried out. At about 325°C. and higher no appreciable amount of ketone can be recovered from the resulting product mixture, whatever combination of the remaining variables employed. On the other hand, useful reaction rates are in general experienced when the temperature exceeds about 225°C.

In addition to temperature, the time at temperature is a primary factor herein. Reference is made to the FIGURE which represents the yield of ketone and of the principal intermediate, a secondary thiol as a function of time. At 315°C. after 40–50 minutes the product contains little or no ketone. For an optimum yield the reaction must be discontinued within a relatively narrow period, i.e., after a duration of from about 13 to 25 minutes. At lower temperatures somewhat longer reaction times are satisfactory. In general, useful reaction times for the instant process are in the range from about 5 to 60 minutes. The shorter reaction times correspond to the use of higher temperatures.

Sulfur is required for the conversion of an olefin to a ketone. It functions as an oxidizing agent in the reaction.

On the other hand, the production of ketone decreases markedly especially at the upper temperatures of the suitable range as the relative amount of sulfur to olefin is raised. Thus, at a ratio of 2:1 under otherwise excellent reaction conditions, i.e., including a temperature of 300°C., there is a marked reduction in ketone production. Broadly the amount of sulfur in the reaction mixture is desirably in the range from about 0.15 to 2.0 mols, and preferably is 0.5 to 1.1 mols per mol of the olefin feed.

Good conversions and yields of olefin to ketone are experienced in the present process in the absence of a basic nitrogen compound. However, the presence of a nitrogen compound, for example ammonia, under otherwise comparable conditions improves the ketone yield by as much as a factor of 2–3. Thus, the nitrogen base acts as a promoter for the process. At least in part the mechanism for this enhancement appears to be in the solubilization of the sulfur by formation of polysulfide sulfur, a soluble form. Other nitrogen bases, as known in the art, including pyridine, alkyl amines, morpholine, and the like, are also satisfactory. However, the use of ammonia is in general preferable because of such factors as cost, ease of removal from the product mixture, and the like.

The amount of the nitrogen base present in the reaction mixture is desirably relatively minor compared to the water or olefin. In general, for each mol of the olefin in the mixture, less than 4 mols of the base should be employed. Best results appear to obtain when the mol ratio of the base per mol of olefin is in the range 0.15–0.75 to 1, respectively.

Water is believed to be polyfunctional in the subject process. At least one mol must be present for each mol of ketone formed. The water is the source of the ketone oxygen. Water also serves as a medium for the reaction. It also appears to participate in the reaction mechanism. Best results are, in general, achieved when about 5 to 20 mols of water are present for each mol of the olefin feed. Satisfactory results obtain at water to olefin ratios in the range from about 2–100 to 1, respectively.

Inert diluents, such as benzene, toluene, alkane mixtures, and alkane-aromatic hydrocarbon mixtures, and the like, may be employed in the subject process. Particularly in the case of a high molecular weight olefin feed, for example an olefinic ethylene polymer, the use of a diluent is desirable in order to present the olefin in the required liquid phase. For an ordinary olefin feed the use of an inert diluent is, in general, not especially advantageous and usually constitutes an unnecessary process cost.

For the satisfactory conversion of a carbon-carbon double bond to a ketone functional group as in the process of the invention, the reactants must be in the liquid phase, that is either in a single homogeneous liquid phase or in two or more well mixed liquid phases, i.e., an aqueous and one or more organic liquid phases. With the exception of olefins having certain requirements noted below, liquefiable olefinic hydrocarbons are, in general, satisfactory feeds for use herein and are contemplated for such employment. By a liquefiable olefinic hycrocarbon feed, as used herein, is meant an olefin or a mixture of olefins which at a temperature within the process range is a liquid or which liquefies upon the addition of an inert liquid diluent.

The conditions in addition to the aforementioned requirements which apply to the feed compounds suitable for use in the process are:

1. The olefin must contain at least 3 carbon atoms, an inherency of the ketone class definition;
2. The olefin must contain a carbon-carbon double bond pair which is not included within a six membered carbocyclic ring (in general, in this case aromatization of the ring preempts ketone formation); and
3. At least one carbon atom of the carbon-carbon double bond pair must be a secondary carbon atom, i.e., be bonded to each of two other carbon atoms.

Best results are in general experienced in the subject process when the olefin contains but a single carbon-carbon double bond. Monoolefinic hydrocarbons and mixtures thereof are consequently preferred as process feeds. Polyolefinic hydrocarbons may also be converted to ketones having more than one carbonyl group, but yields appear to be inferior relative to those obtained by the use of the monoolefinic feeds.

In addition to the process feed types defined by the above-noted references, certain substituent groups, inert substituents, are not adversely affected by the process conditions. Thus, a hydrogen atom attached to a remote carbon atom of an otherwise olefinic hydrocarbon feed may be replaced by an inert substituent. Carboxyl ($-CO_2H$), and carboxamide ($-CONH_2$) groups, are in general not adversely affected by the present process conditions. Usually the feed compounds desirably contain no more than two inert substituent groups.

With reference to an olefinic feed compound for the present process and as used herein, by a remote carbon is meant by definition a carbon atom having at least one intervening carbon atom between it and a carbon-carbon double bond of the compound.

Representative olefinic hydrocarbons useful as feed compounds for the process include propene, butene-1, butene-2, 1-tetradecene, 2-pentadecene, 5-hexadecene, 6-heptadecene, 1-eicosene, 1-tetracontene, 1-pentacontene, 4-methylpentene-1, 5,6-dimethyloctene-1, 5-cyclohexyldecene-1, 8-phenyloctene-1, 7-($\alpha$naphthyl)-heptene-2, cyclopentene, cyclooctene, cyclooctadiene, cyclododecene, 1,5,9,-cyclododecatriene, 1,5-hexadiene, 1,7-octadiene, 4,4-dimethylheptadiene-1,6, 5-(p-tolyl)-pentene-1, 4-pentenoic acid, 5-hexenoic acid amide and the like olefinic feed compounds. The n-alkenes having a carbon atom content in the range 3 to 20 and mixtures thereof are particularly preferred feeds since the ketones resulting from the conversion of these n-alkenes are especially useful solvent media.

PREFERRED EMBODIMENT

In a preferred embodiment of my process, 1-octene is converted to octanone. The reaction is carried out continuously in a tube-type reactor capable of operation at a pressure of about 150 atm., which is maintained at about 300°C. by a suitable indirect heat exchanger. The dimensions of the reactor are proportioned to result, when taken in conjunction with the feed rate of the reactants to the unit, in an average contact time at temperature of about 15 mins. For each mol of 1-octene about 10 mols of water, 0.15 mol of hydrogen sulfide, 0.7 mol of sulfur and 0.25 mol of ammonia are fed to the reactor. Sufficient free space (about 5% of the total volume of the liquid feed) is provided to accommodate expansion effects. The pressure let-down unit and product receiver provides for flash cooling of the product stream, including separation of the organic and aqueous portions from the recyclable hydrogen sulfide-ammonia fraction, and separation of the organic and aqueous phases.

The aqueous phase contains a minor amount of the desired octanone and for maximum yield this is recovered by extraction and is added to the main organic product fraction.

The separated organic phase is a mixture and contains unconverted octene, octanone, octanethiol and dioctyl sulfide. Typically on a 1-pass basis the conversion of the alkene is about 92% and the yield of octanone is about 51 weight percent (based upon octene converted), of octanethiol is about 39 weight percent and of the sulfide is about 8 weight percent. Upon a continuous basis with recycle of the thiol and sulfide the yield of octanone is roughly 90 mol percent. A minor amount (less than 5 mol percent) of cyclic impurity identified as a mixture of thiophene and tetrahydrothiophene compounds is also present in the product. These compounds may be removed from the octanone product by an efficient fractional distillation or by a suitable chemical treatment and distillation. The resulting ketone is a high purity mixture which is mainly 2-octanone and 3-octanone and which contains a minor amount of 4-octanone (usually less than about 5 mol percent).

The following examples further illustrate the invention.

EXAMPLES 1–7:

These examples were carried out in a pressure autoclave reactor for a period of 15 mins. at a temperature of 300°C., the mol ratio of the charge, olefinic hydrocarbon:sulfur:ammonia: hydrogen sulfide:water was 1.0:0.63:0.6:0.5:16, respectively, with the following results.

| Example No. | Olefin Feed | Conversion Percent | Ketone Yield Weight Percent |
| --- | --- | --- | --- |
| 1 | 1-Hexene | 88 | 51 |
| 2 | 1-Octene | 83 | 61 |
| 3 | 2-Octene | 80 | 65 |
| 4 | 1-Decene | 80 | 59 |
| 5 | 1-Dodecene | 80 | 56 |
| 6 | Cyclooctene | 81 | 59 |

| Example No. | Olefin Feed | Conversion Percent | Ketone Yield Weight Percent |
|---|---|---|---|
| 7 | Cyclododec-ene | 67 | 38 |

In addition to the indicated yield of ketone product, the balance of the materials in the product stream consisted of unconverted and partially isomerized olefin as well as the corresponding secondary thiol and sulfide in relative amounts similar to those described in the preferred embodiment herein.

The foregoing results demonstrate that olefinic hydrocarbons are readily converted to corresponding ketones by the process of the present invention.

When a feed compound in which the carbon-carbon double bond is part of a six-membered carbocyclic ring is employed in the process under similar conditions, little or no ketone is produced, rather the ring is converted to a benzene ring by oxidative dehydrogenation.

EXAMPLE 8-9:

The ketone product from Examples 2 and 3 were analyzed by Nuclear Magnetic Resonance using appropriate standards and the product distribution was as follows:

| Starting Olefin | x-Octanone, Wt. % | | |
|---|---|---|---|
| | 2 | 3 | 4 |
| 1-Octene | 76 | 20 | 4 |
| 2-Octene | 41 | 52 | 7 |

These data demonstrate that the production of ketone in the present process in not specific to 1-alkene feeds, but that on the contrary internal alkenes are in general useful process feeds except that, as noted above, the carbon-carbon double bond cannot be included as a component of a six-membered carbocyclic ring. The presence of the 4-octanone isomer in the products as well as the observation that the unconverted olefin feed contains carbon-carbon double bond isomerized alkene indicates that the double bond of compounds such as 2,3-dimethyl-2-pentene and analogous alkenes where both carbon atoms of the double bond are tertiary carbons isomerize and yield the isomeride product, i.e., 2,3-dimethyl-4-pentanone.

EXAMPLES 10-11:

The alkanethiol and dialkyl sulfide by-products from Examples 1 and 2 were used as feeds under the process conditions of the original reaction with the following comparative results:

| Example No. | Olefin Feed | Yield, Wt. % | |
|---|---|---|---|
| | | Hexa-none | Octanone |
| 1 | 1-Hexene | 51 | |
| 10 | Recycle Feed | 42 | |
| 2 | 1-Octene | | 51 |
| 11 | Recycle Feed | | 47 |

These examples illustrate that the recycle of intermediate thiol and sulfide by-products can be employed as a means to markedly improve the results achievable by the process of the invention. They also establish that alkanethiol and dialkyl sulfides and mixtures thereof are useful primary feed compounds for the production of ketones under the conditions of the subject invention where the compound is liquifiable at a temperature within the process range and is of the formula R—S$_n$—R' wherein R is a hydrocarbon group and R' is hydrogen or a hydrocarbon group and $n$ is an integer in the range of 1 to 10, and wherein the sulfur atom attachment to at least one of R or R' is via a secondary carbon atom which is not included as a member of a six-membered carbocyclic ring.

EFFECT OF AMMONIA

EXAMPLES 12-14:

The effect of variation in the relative amount of ammonia upon the process results was demonstrated. These runs were carried out in the manner as in Examples 1-7 using 1-octene as the feed with the olefin:sulfur:hydrogen sulfide:water mol ratio of 1:0.7:0.4:12, respectively, and with the ammonia as indicated below in the Table of results.

| Example No. | NH$_3$, Mols | Conversion, % | Yield, Wt. % |
|---|---|---|---|
| 12 | 0.6 | 92 | 51 |
| 13 | 1.1 | 86 | 44 |
| 14 | 0 | 81 | 27 |

The foregoing examples demonstrate that the action of a nitrogen base is not essential for the direct production of ketones by the process. On the other hand, the presence of a nitrogen base does substantially improve the results.

EFFECT OF HYDROGEN SULFIDE

EXAMPLES 15-16:

The effect of variation in the relative amount of hydrogen sulfide upon the process results was illustrated. These runs were carried out in the manner as in Examples 1-7 using 1-octene as the representative feed with the olefin: sulfur: ammonia:water mol ratio of 1:0.7:0.6:12, respectively, and with the hydrogen sulfide as indicated below in the Table of results.

| Example No. | H$_2$S, Mols | Conversion, % | Yield, Wt. % |
|---|---|---|---|
| 15 | 0.40 | 92 | 51 |
| 16 | 0.15 | 92 | 49 |

These results illustrate that large variations in the relative amount of hydrogen sulfide in the process feed does not materially affect the results. The difference in the yield figure is believed to be significant in view of these and other examples. Therefore, hydrogen sulfide appears to be a promoter in the reaction system. Useful relative amounts of hydrogen sulfide to olefin feed are in the range 0.05-0.75 mol per mol of olefin.

PRODUCT PURIFICATION

Where the process feed is a mixture of olefins having a range of molecular weights, distillation is usually ineffective as a means for satisfactory recovery of the ketone product because the range of thiol intermediates will have boiling points within the boiling point range of the ketone product. In this event a convenient means to facilitate product purification is demonstrated in the following example. By conversion of the thiol intermediates to sulfides, $$2RSH + mS° \rightarrow RS_nR + H_2S\uparrow,$$

in a reaction effected at a moderate (below 100°C.) or at the ambient temperature.

EXAMPLE 17

In the manner as described in Example 1, a 1-octene feed was converted to ketone. The product mixture comprised 0.31 mol of unconverted octenes, 1.14 mols of octanones, 0.85 mol of octyl thiol and 0.69 mol of octyl sulfide. The mixture was efficiently contacted with several aliquots of concentrated aqueous ammonia reagent (400 mls total) containing sulfur (7 mols per liter). The separated organic layer was dried. The octenes and octanones were fractionally distilled out of the dried product mixture and contained no octyl thiol. The bottoms from the distillation contained octyl sulfides and no thiol.

This example demonstrates that thiols present in a ketone mixture can be readily and efficiently separated from the mixture by conversion to the corresponding sulfide by contacting the mixture with aqueous ammonium or alkali metal polysulfide and fractional distillation of the treated organic mixture.

EXAMPLE 18

The octyl sulfide mixture recovered in Example 17 contained, on the basis of the analysis for sulfur, 12.5% (weight) of mono-, 22.2% of di- and 80% octyl trisulfide. A portion of the above octyl sulfide mixture together with a portion of the recovered octene was charged to a sealable pressure reactor together with water, ammonia and hydrogen sulfide. The reactor and contents were heated at 300°C. for a period of 15 minutes. Based upon the octene and sulfide feed, the yields of octanones and octyl thiol were 46.5 and 34% (weight).

This example illustrates that organic sulfides are readily and satisfactorily converted by the present process into a mixture of ketones and recyclable by-product.

It will be readily appreciated from the foregoing disclosure and examples that variations can be made by those skilled in the art without departing from the scope and spirit of the appended claims.

I claim:

1. The process for the conversion of a feed hydrocarbon having a single carbon-carbon double bond to a ketone having the same carbon atom content as said feed, which comprises maintaining in the liquid phase a mixture of the feed, water, and sulfur at a temperature in the range from about 225° to 325°C. for a period sufficient to produce an appreciable amount of said ketone, wherein for each mol of the feed the mixture contains an amount of sulfur in the range from about 0.15 to 2 mols, and an amount of water in the range from about 2 to 100 mols, said period being in the range from about 5 to 60 minutes; wherein said feed contains at least 3 carbon atoms, at least one carbon atom of the carbon-carbon double bond pair is a secondary carbon, said pair is not included in a six-membered carbocyclic ring, said feed is liquefiable at a temperature within said range, and said feed is either an n-alkene or a cycloalkene; and wherein said conversion is promoted by inclusion of 0.05 to 0.75 mol hydrogen sulfide in the mixture for each mol of olefin present.

* * * * *